(12) United States Patent
Gohde

(10) Patent No.: US 11,896,778 B2
(45) Date of Patent: Feb. 13, 2024

(54) CATHETER INSERTION-TRAY SYSTEMS AND METHODS THEREOF

(71) Applicant: C. R. Bard, Inc., Murray Hill, NJ (US)

(72) Inventor: John Gohde, Decatur, GA (US)

(73) Assignee: C. R. Bard, Inc., Franklin Lakes, NJ (US)

( * ) Notice: Subject to any disclaimer, the term of this patent is extended or adjusted under 35 U.S.C. 154(b) by 681 days.

(21) Appl. No.: 16/497,770

(22) PCT Filed: Mar. 29, 2018

(86) PCT No.: PCT/US2018/025260
§ 371 (c)(1),
(2) Date: Sep. 25, 2019

(87) PCT Pub. No.: WO2018/183752
PCT Pub. Date: Oct. 4, 2018

(65) Prior Publication Data
US 2021/0100978 A1 Apr. 8, 2021

Related U.S. Application Data

(60) Provisional application No. 62/479,687, filed on Mar. 31, 2017.

(51) Int. Cl.
*A61M 25/01* (2006.01)
*A61M 25/00* (2006.01)
(Continued)

(52) U.S. Cl.
CPC ......... *A61M 25/0111* (2013.01); *A61B 42/10* (2016.02); *A61B 46/23* (2016.02);
(Continued)

(58) Field of Classification Search
CPC .......... A61M 25/0111; A61M 25/0017; A61M 25/002; A61M 2207/00;
(Continued)

(56) References Cited

U.S. PATENT DOCUMENTS

| 935,419 A | 9/1909 | Smith |
|---|---|---|
| 2,346,636 A | 4/1944 | Porter |

(Continued)

FOREIGN PATENT DOCUMENTS

| CN | 1511014 A | 7/2004 |
|---|---|---|
| CN | 201823147 U | 5/2011 |

(Continued)

OTHER PUBLICATIONS

"Arrow International, Inc. Introduces Maximal Barrier Precautions Tray", Press release. Jan. 11, 2006.

(Continued)

*Primary Examiner* — Nicholas J. Weiss
*Assistant Examiner* — Brandon W. Levy
(74) *Attorney, Agent, or Firm* — Rutan & Tucker LLP

(57) ABSTRACT

A catheterization package including a catheterization tray and contents for a catheterization procedure. The catheterization tray can include a structural configuration for maintaining a sterile field about a patient throughout the catheterization procedure, the sterile field including at least a portion of the tray. The structural configuration of the tray can provide a sterile side of the tray designated for a first person performing sterile steps of the catheterization procedure in the sterile field. The structural configuration of the tray can also provide a non-sterile side of the tray designated for either the first person or a second person performing non-sterile steps of the catheterization procedure outside the sterile field. The contents for the catheterization procedure can include a perineal care kit, two or more pairs of gloves, and a drainage system including a catheter.

22 Claims, 6 Drawing Sheets

Figure 1:
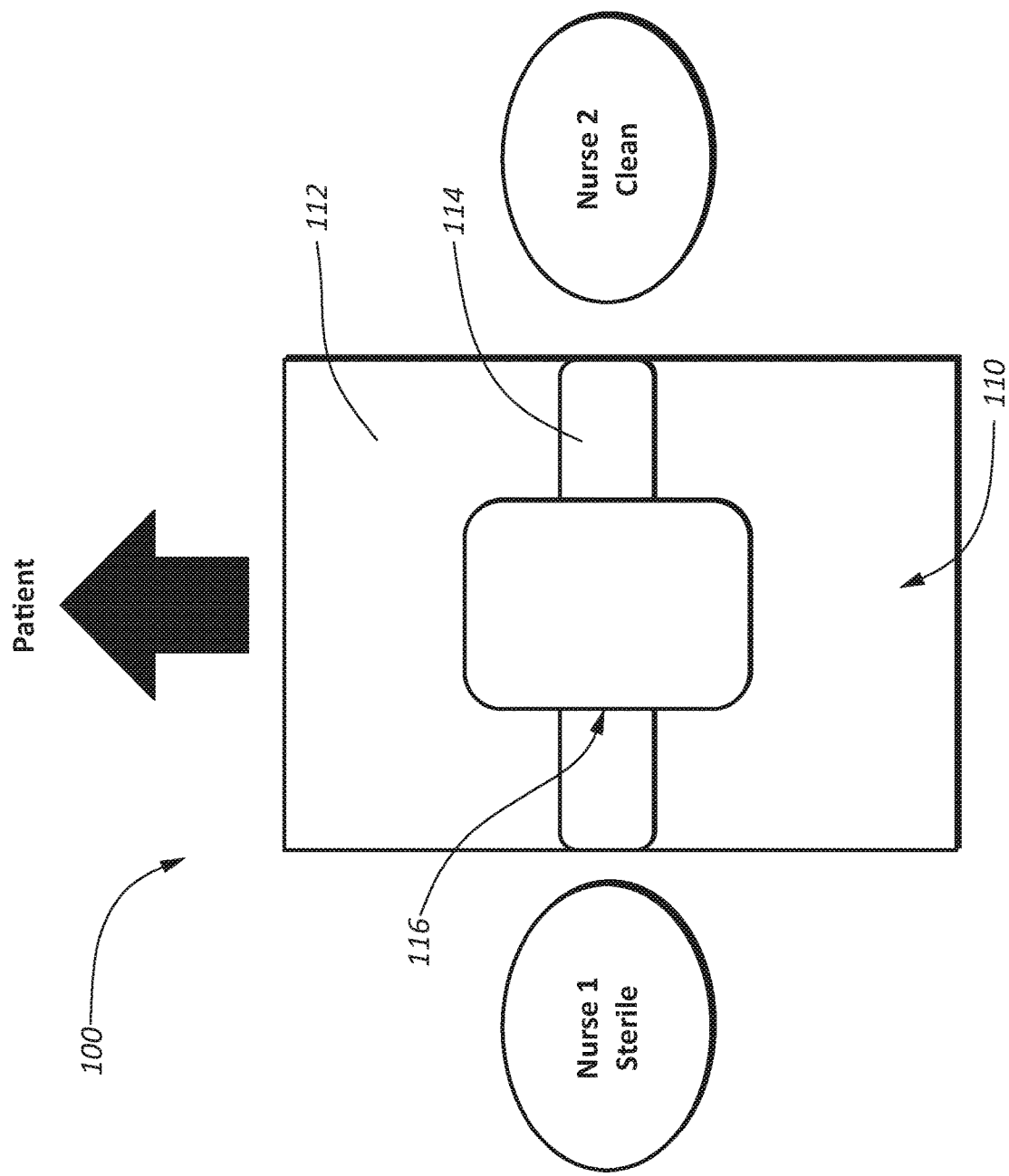

(51) Int. Cl.
  *A61B 42/10* (2016.01)
  *A61B 46/23* (2016.01)
  *A61B 46/00* (2016.01)
(52) U.S. Cl.
  CPC ........... *A61B 46/30* (2016.02); *A61M 25/002* (2013.01); *A61M 25/0017* (2013.01); *A61B 2046/234* (2016.02); *A61M 2207/00* (2013.01); *A61M 2210/1085* (2013.01)
(58) Field of Classification Search
  CPC ....... A61M 2210/1085; A61M 25/0113; A61B 42/10; A61B 46/23; A61B 46/30; A61B 2046/234; A61B 2050/3008; A61B 46/20; A61B 42/00; A61B 42/40; A61B 46/00; A61B 50/33; A61B 34/25; A61B 2034/252; A61B 2090/0807; A61B 50/30; B65D 1/36
  See application file for complete search history.

(56) References Cited

U.S. PATENT DOCUMENTS

| | | | |
|---|---|---|---|
| 2,659,485 A | 11/1953 | Duley et al. |
| 2,874,707 A | 2/1959 | Koppel |
| 2,947,415 A | 8/1960 | Garth |
| 3,107,786 A | 10/1963 | Adelman |
| 3,137,387 A | 6/1964 | Overment |
| 3,138,253 A | 6/1964 | Harautuneian |
| 3,144,932 A | 8/1964 | Zerbo, Jr. |
| 3,166,189 A | 1/1965 | Disston |
| 3,324,855 A | 6/1967 | Heimlich |
| 3,329,261 A | 7/1967 | Serany, Jr. et al. |
| 3,345,988 A | 10/1967 | Vitello |
| 3,379,339 A | 4/1968 | Asenbauer |
| 3,485,352 A | 12/1969 | Pilger |
| D218,077 S | 7/1970 | Gabriel |
| 3,542,019 A | 11/1970 | Gittins |
| 3,580,475 A | 5/1971 | Mobley |
| D222,312 S | 10/1971 | Kurtz et al. |
| 3,642,123 A | 2/1972 | Knox |
| 3,650,393 A | 3/1972 | Reiss et al. |
| 3,726,281 A | 4/1973 | Norton et al. |
| 3,762,399 A | 10/1973 | Riedell |
| 3,770,119 A | 11/1973 | Hultberg et al. |
| 3,802,555 A | 4/1974 | Grasty et al. |
| 3,851,649 A | 12/1974 | Villari |
| D234,404 S | 2/1975 | Merril |
| 3,901,235 A | 8/1975 | Patel et al. |
| D237,315 S | 10/1975 | Nowakowski |
| D237,317 S | 10/1975 | Nowakowski |
| 3,965,900 A | 6/1976 | Boedecker |
| 3,967,728 A | 7/1976 | Gordon et al. |
| 3,976,195 A | 8/1976 | Cohen |
| 3,978,983 A | 9/1976 | Brezette |
| 3,981,398 A | 9/1976 | Boshoff |
| D242,654 S | 12/1976 | Rawls |
| 3,998,221 A | 12/1976 | Collins |
| D243,798 S | 3/1977 | Swartz |
| 4,011,944 A | 3/1977 | Cooley et al. |
| 4,053,280 A | 10/1977 | Salisbury |
| 4,085,845 A | 4/1978 | Perfect |
| D248,871 S | 8/1978 | Forsman et al. |
| D249,362 S | 9/1978 | Forsman et al. |
| 4,140,127 A | 2/1979 | Cianci et al. |
| 4,149,635 A | 4/1979 | Stevens |
| 4,153,160 A | 5/1979 | Leigh |
| 4,160,505 A | 7/1979 | Rauschenberger |
| 4,170,300 A | 10/1979 | Pick |
| 4,226,328 A | 10/1980 | Beddow |
| 4,256,225 A | 3/1981 | Jackson |
| 4,262,800 A | 4/1981 | Nethercutt |
| 4,266,669 A | 5/1981 | Watson |
| D262,995 S | 2/1982 | Gaba et al. |
| 4,332,322 A | 6/1982 | Jaeschke et al. |
| 4,334,537 A | 6/1982 | Peterson |
| 4,366,901 A | 1/1983 | Short |
| D268,130 S | 3/1983 | Easton |
| 4,458,705 A | 7/1984 | Cawood |
| D275,886 S | 10/1984 | Sheward et al. |
| D276,462 S | 11/1984 | Villarreal |
| D277,508 S | 2/1985 | Clair |
| 4,501,363 A | 2/1985 | Isbey, Jr. |
| 4,522,302 A | 6/1985 | Paikoff |
| 4,523,679 A | 6/1985 | Paikoff et al. |
| 4,530,349 A | 7/1985 | Metzger |
| D280,663 S | 9/1985 | Albon et al. |
| D280,933 S | 10/1985 | McLaughlin |
| D283,051 S | 3/1986 | Fichera |
| 4,595,102 A | 6/1986 | Cianci et al. |
| D287,760 S | 1/1987 | Discko, Jr. |
| 4,767,008 A | 8/1988 | Warnecke et al. |
| 4,795,441 A | 1/1989 | Bhatt |
| 4,811,847 A | 3/1989 | Reif et al. |
| 4,828,113 A | 5/1989 | Friedland et al. |
| 4,844,259 A | 7/1989 | Glowczewskie, Jr. et al. |
| 4,858,821 A | 8/1989 | Bickelhaupt |
| 4,925,448 A | 5/1990 | Bazaral |
| 4,928,830 A | 5/1990 | Brewer |
| 4,944,427 A | 7/1990 | Yamada et al. |
| D310,896 S | 9/1990 | Winjum |
| 4,989,733 A | 2/1991 | Patry |
| 5,007,535 A | 4/1991 | Meseke et al. |
| 5,024,326 A | 6/1991 | Sandel et al. |
| 5,031,768 A | 7/1991 | Fischer |
| 5,098,391 A | 3/1992 | Pantages et al. |
| 5,163,557 A | 11/1992 | Sokolowski |
| 5,170,804 A | 12/1992 | Glassman |
| 5,174,306 A | 12/1992 | Marshall |
| D334,973 S | 4/1993 | Valentine et al. |
| D337,830 S | 7/1993 | Coyne et al. |
| 5,242,398 A | 9/1993 | Knoll et al. |
| D343,687 S | 1/1994 | Houghton et al. |
| 5,306,239 A | 4/1994 | Gurmarnik et al. |
| 5,318,543 A | 6/1994 | Ross et al. |
| 5,322,163 A | 6/1994 | Foos |
| 5,339,955 A | 8/1994 | Horan et al. |
| D351,661 S | 10/1994 | Fischer |
| D353,078 S | 12/1994 | Davis et al. |
| 5,384,103 A | 1/1995 | Miller |
| 5,392,918 A | 2/1995 | Harrison |
| 5,394,983 A | 3/1995 | Latulippe et al. |
| 5,449,071 A | 9/1995 | Levy |
| 5,525,314 A | 6/1996 | Hurson |
| 5,586,163 A | 12/1996 | Goldstein |
| 5,590,778 A | 1/1997 | Dutchik |
| D380,272 S | 6/1997 | Partika et al. |
| D387,177 S | 12/1997 | Davis |
| D387,559 S | 12/1997 | Williamson |
| 5,704,914 A | 1/1998 | Stocking et al. |
| 5,752,234 A | 5/1998 | Withers |
| 5,779,053 A | 7/1998 | Partika et al. |
| 5,810,738 A | 9/1998 | Thomas, II |
| 5,931,303 A | 8/1999 | Salvadori |
| 5,941,241 A | 8/1999 | Weinstein et al. |
| 5,947,284 A | 9/1999 | Foster |
| 5,947,890 A | 9/1999 | Spencer et al. |
| 5,975,295 A | 11/1999 | Diamond |
| 6,004,136 A | 12/1999 | Ehrenpreis |
| 6,012,586 A * | 1/2000 | Misra .................. A61B 50/30 206/370 |
| 6,068,121 A | 5/2000 | McGlinch |
| 6,090,075 A | 7/2000 | House |
| 6,121,165 A | 9/2000 | Mackey et al. |
| 6,142,152 A | 11/2000 | Gawarecki |
| 6,158,437 A | 12/2000 | Vagley |
| D437,941 S | 2/2001 | Frattini |
| D442,697 S | 5/2001 | Hajianpour |
| D445,198 S | 7/2001 | Frattini |
| D450,130 S | 11/2001 | Goldstein |
| D450,391 S | 11/2001 | Hunt et al. |
| 6,382,212 B1 | 5/2002 | Borchard |
| 6,405,863 B1 | 6/2002 | Dhindsa |
| 6,412,639 B1 | 7/2002 | Hickey |

(56) References Cited

U.S. PATENT DOCUMENTS

| | | |
|---|---|---|
| 6,454,097 B1 | 9/2002 | Blanco |
| 6,502,699 B1 | 1/2003 | Watson |
| D471,640 S | 3/2003 | McMichael et al. |
| D471,641 S | 3/2003 | McMichael et al. |
| 6,579,271 B1 | 6/2003 | Aruffo et al. |
| D480,816 S | 10/2003 | McMichael et al. |
| 6,640,976 B1 | 11/2003 | Franks-Farah et al. |
| 6,681,933 B1 | 1/2004 | Demsien et al. |
| 6,716,200 B2 | 4/2004 | Bracken et al. |
| 6,769,546 B2 | 8/2004 | Busch |
| D495,491 S | 9/2004 | Ramirez et al. |
| D495,807 S | 9/2004 | Agbodoe et al. |
| 6,793,078 B2 | 9/2004 | Roshdy |
| 6,840,379 B2 | 1/2005 | Franks-Farah et al. |
| 6,896,141 B2 | 5/2005 | McMichael et al. |
| 6,907,992 B2 | 6/2005 | McMichael et al. |
| 6,910,581 B2 | 6/2005 | McMichael et al. |
| 6,915,901 B2 | 7/2005 | Feinberg et al. |
| 6,926,708 B1 | 8/2005 | Franks-Farah et al. |
| 6,948,742 B2 | 9/2005 | Buck |
| 6,959,808 B2 | 11/2005 | Discko, Jr. |
| 6,991,096 B2 | 1/2006 | Gottlieb et al. |
| 7,048,120 B2 | 5/2006 | Pond |
| 7,066,328 B2 | 6/2006 | Pulsifer |
| 7,100,771 B2 | 9/2006 | Massengale et al. |
| D530,920 S | 10/2006 | Snell |
| 7,131,965 B1 | 11/2006 | Thornbury et al. |
| D547,064 S | 7/2007 | Snell |
| D549,454 S | 8/2007 | Ahman |
| 7,264,869 B2 | 9/2007 | Tobita et al. |
| 7,278,987 B2 | 10/2007 | Solazzo |
| D557,047 S | 12/2007 | Dretzka |
| D561,473 S | 2/2008 | Phillips et al. |
| D563,673 S | 3/2008 | Dretzka |
| 7,401,703 B2 | 7/2008 | McMichael et al. |
| 7,410,053 B2 | 8/2008 | Bowen et al. |
| 7,434,687 B2 | 10/2008 | Itou et al. |
| D579,662 S | 11/2008 | Dretzka |
| 7,491,176 B2 | 2/2009 | Mann |
| 7,494,487 B2 | 2/2009 | Timm |
| D590,596 S | 4/2009 | Dretzka |
| D596,311 S | 7/2009 | Antons |
| 7,624,869 B2 | 12/2009 | Primer |
| 7,634,893 B2 | 12/2009 | Gottlieb et al. |
| D609,819 S | 2/2010 | Tomes et al. |
| 7,662,146 B2 | 2/2010 | House |
| D612,153 S | 3/2010 | Liao |
| 7,671,014 B2 | 3/2010 | Beals et al. |
| D613,418 S | 4/2010 | Ryan et al. |
| D618,821 S | 6/2010 | Larsen |
| 7,743,918 B2 | 6/2010 | Itou et al. |
| 7,785,312 B2 | 8/2010 | Thorne, Jr. et al. |
| D623,765 S | 9/2010 | Tomes et al. |
| D631,558 S | 1/2011 | Harmston et al. |
| D636,894 S | 4/2011 | Tomes et al. |
| D638,137 S | 5/2011 | Gross et al. |
| 7,993,326 B2 | 8/2011 | Massengale et al. |
| D646,796 S | 10/2011 | Walter |
| D650,912 S | 12/2011 | Tomes et al. |
| 8,128,595 B2 | 3/2012 | Walker et al. |
| 8,177,064 B2 | 5/2012 | McCormick et al. |
| D662,218 S | 6/2012 | Pittman |
| 8,240,468 B2 | 8/2012 | Wilkinson et al. |
| 8,273,312 B2 | 9/2012 | Porat et al. |
| 8,282,829 B2 | 10/2012 | Yu et al. |
| 8,448,786 B2 | 5/2013 | Tomes et al. |
| D688,461 S | 8/2013 | Ambrefe, Jr. et al. |
| 8,584,849 B2 | 11/2013 | McCaffrey |
| 8,597,505 B2 | 12/2013 | Fulkerson et al. |
| 8,628,549 B2 | 1/2014 | To et al. |
| 8,631,935 B2 | 1/2014 | Tomes et al. |
| 8,656,929 B2 | 2/2014 | Miller et al. |
| 8,662,306 B2 | 3/2014 | Agrawal |
| 8,678,190 B2 | 3/2014 | Tomes et al. |
| 8,708,999 B2 | 4/2014 | Hong et al. |
| D704,856 S | 5/2014 | Tomes et al. |
| D707,848 S | 6/2014 | Shigeno et al. |
| 8,746,452 B2 | 6/2014 | Tomes et al. |
| D708,347 S | 7/2014 | Lober |
| D708,759 S | 7/2014 | Heyman et al. |
| 8,875,940 B2 | 11/2014 | Danchisin et al. |
| D720,470 S | 12/2014 | Lober |
| D720,471 S | 12/2014 | Angel et al. |
| 9,084,593 B2 | 7/2015 | Yakel et al. |
| D738,491 S | 9/2015 | Foley et al. |
| 9,162,781 B2 | 10/2015 | Lien |
| 9,186,217 B2 | 11/2015 | Goyal |
| D751,726 S | 3/2016 | Nishioka et al. |
| 9,283,352 B2 | 3/2016 | Tomes et al. |
| 9,486,604 B2 | 11/2016 | Murray et al. |
| 9,522,001 B2 | 12/2016 | Bui et al. |
| 9,522,753 B2 | 12/2016 | Tomes et al. |
| 9,693,756 B2 | 7/2017 | Tomes et al. |
| 9,744,333 B2 | 8/2017 | Terzibashian |
| 9,745,088 B2 | 8/2017 | Tomes et al. |
| 9,795,761 B2 | 10/2017 | Lockwood et al. |
| 9,808,400 B2 | 11/2017 | Tomes et al. |
| 9,808,596 B2 | 11/2017 | Tomes et al. |
| 9,872,969 B2 | 1/2018 | Conway et al. |
| 10,022,464 B2 | 7/2018 | Sarphati et al. |
| 10,039,897 B2 | 8/2018 | Norris et al. |
| 10,106,295 B2 | 10/2018 | Lockwood |
| 10,251,812 B2 | 4/2019 | Tomes et al. |
| 10,512,752 B2 | 12/2019 | Tomes et al. |
| 10,639,120 B2 | 5/2020 | Turturro et al. |
| 2002/0185406 A1 | 12/2002 | Massengale et al. |
| 2003/0038475 A1 | 2/2003 | Stancil |
| 2003/0060761 A1 | 3/2003 | Evans et al. |
| 2003/0075474 A1 | 4/2003 | Moyer et al. |
| 2003/0159966 A1 | 8/2003 | McMichael et al. |
| 2003/0159967 A1 | 8/2003 | McMichael et al. |
| 2003/0159968 A1 | 8/2003 | McMichael et al. |
| 2003/0159969 A1 | 8/2003 | McMichael et al. |
| 2003/0211627 A1 | 11/2003 | Koesterman et al. |
| 2004/0004019 A1 | 1/2004 | Busch |
| 2004/0055919 A1 | 3/2004 | Rowe et al. |
| 2004/0060260 A1 | 4/2004 | Gottlieb et al. |
| 2004/0111072 A1 | 6/2004 | McKissick |
| 2004/0161732 A1 | 8/2004 | Stump et al. |
| 2004/0180822 A1 | 9/2004 | Grafton |
| 2004/0195145 A1 | 10/2004 | Roshdy |
| 2004/0200754 A1 | 10/2004 | Hagemeier |
| 2004/0238391 A1 | 12/2004 | Pond |
| 2005/0022822 A1 | 2/2005 | Santilli et al. |
| 2005/0098470 A1 | 5/2005 | Davis et al. |
| 2005/0101905 A1 | 5/2005 | Merry |
| 2005/0236940 A1 | 10/2005 | Rockoff |
| 2005/0256453 A1 | 11/2005 | Nagamatsu |
| 2005/0285385 A1 | 12/2005 | Bova et al. |
| 2006/0009742 A1 | 1/2006 | Solazzo |
| 2006/0086634 A1 | 4/2006 | Steppe |
| 2006/0104857 A1 | 5/2006 | Pigott et al. |
| 2006/0186010 A1 | 8/2006 | Warnack et al. |
| 2006/0205996 A1* | 9/2006 | Presthus ............... A61B 90/11 600/29 |
| 2006/0224086 A1 | 10/2006 | Harty |
| 2006/0264822 A1 | 11/2006 | Nagamatsu |
| 2006/0271019 A1 | 11/2006 | Stoller et al. |
| 2006/0282045 A1 | 12/2006 | Wilkinson et al. |
| 2007/0026472 A1 | 2/2007 | Prokash et al. |
| 2007/0049806 A1 | 3/2007 | Adams et al. |
| 2007/0060908 A1 | 3/2007 | Webster et al. |
| 2007/0084742 A1 | 4/2007 | Miller et al. |
| 2007/0088330 A1 | 4/2007 | House |
| 2007/0095699 A1 | 5/2007 | Frieze et al. |
| 2007/0142786 A1 | 6/2007 | Lampropoulos et al. |
| 2007/0156099 A1 | 7/2007 | Fowler |
| 2007/0161971 A1 | 7/2007 | House |
| 2007/0197998 A1 | 8/2007 | Itou et al. |
| 2007/0225687 A1 | 9/2007 | House |
| 2007/0273258 A1 | 11/2007 | Ernst |
| 2007/0299431 A1 | 12/2007 | Jakubowski et al. |
| 2008/0045861 A1 | 2/2008 | Miller et al. |
| 2008/0058725 A1 | 3/2008 | Scribner et al. |

(56) References Cited

U.S. PATENT DOCUMENTS

| | | |
|---|---|---|
| 2008/0116106 A1 | 5/2008 | Lampropoulos et al. |
| 2008/0121553 A1 | 5/2008 | Gobel |
| 2008/0125722 A1 | 5/2008 | Hess et al. |
| 2008/0172042 A1 | 7/2008 | House |
| 2008/0221515 A1 | 9/2008 | Nagamatsu |
| 2008/0249482 A1 | 10/2008 | Erez |
| 2008/0272023 A1 | 11/2008 | McCormick et al. |
| 2008/0283426 A1 | 11/2008 | Primer et al. |
| 2008/0283433 A1 | 11/2008 | Primer |
| 2009/0026146 A1 | 1/2009 | Carlisle et al. |
| 2009/0076461 A1 | 3/2009 | Susi et al. |
| 2009/0184026 A1 | 7/2009 | Massengale et al. |
| 2009/0194453 A1 | 8/2009 | Thorne, Jr. et al. |
| 2009/0208368 A1 | 8/2009 | Waldrep et al. |
| 2009/0234346 A1 | 9/2009 | McBride, Jr. et al. |
| 2009/0236259 A1 | 9/2009 | Hicks |
| 2010/0274205 A1 | 10/2010 | Morelli et al. |
| 2010/0307941 A1 | 12/2010 | Tomes et al. |
| 2010/0307942 A1 | 12/2010 | Tomes et al. |
| 2010/0311026 A1 | 12/2010 | Tomes et al. |
| 2011/0107494 A1 | 5/2011 | Haines |
| 2011/0120906 A1 | 5/2011 | Umholtz et al. |
| 2011/0155599 A1 | 6/2011 | Yakel et al. |
| 2011/0203957 A1 | 8/2011 | Zoland et al. |
| 2011/0232234 A1 | 9/2011 | Lockwood et al. |
| 2011/0233079 A1 | 9/2011 | Macinnes et al. |
| 2011/0284410 A1 | 11/2011 | Lockwood |
| 2011/0290260 A1 | 12/2011 | Tomes et al. |
| 2011/0290262 A1 | 12/2011 | Tomes et al. |
| 2011/0297147 A1 | 12/2011 | Lick et al. |
| 2012/0145589 A1 | 6/2012 | Macinnes et al. |
| 2012/0150123 A1 | 6/2012 | Lawrence et al. |
| 2012/0222686 A1 | 9/2012 | Lockwood et al. |
| 2012/0271161 A1 | 10/2012 | Buckberry |
| 2012/0298114 A1* | 11/2012 | Landsman ............ A61M 25/02 604/385.03 |
| 2013/0037440 A1 | 2/2013 | Danchisin et al. |
| 2013/0042576 A1 | 2/2013 | Sweeney |
| 2013/0245496 A1 | 9/2013 | Wells et al. |
| 2013/0269713 A1 | 10/2013 | Bui et al. |
| 2013/0277248 A1 | 10/2013 | Tomes et al. |
| 2013/0277262 A1 | 10/2013 | Nemard |
| 2014/0021087 A1 | 1/2014 | Adler et al. |
| 2014/0039349 A1 | 2/2014 | Moghe et al. |
| 2014/0100551 A1 | 4/2014 | Holmstrom |
| 2014/0142465 A1 | 5/2014 | Tomes et al. |
| 2014/0231287 A1 | 8/2014 | Tomes et al. |
| 2014/0231288 A1 | 8/2014 | Tomes et al. |
| 2014/0262851 A1 | 9/2014 | Adler et al. |
| 2014/0263595 A1 | 9/2014 | Pantelleria |
| 2015/0048103 A1 | 2/2015 | Danchisin et al. |
| 2015/0083627 A1 | 3/2015 | Gorman |
| 2015/0151017 A1 | 6/2015 | Tipton et al. |
| 2015/0258304 A1 | 9/2015 | Tomes et al. |
| 2015/0283354 A1 | 10/2015 | Olson et al. |
| 2015/0335855 A1 | 11/2015 | Tomes et al. |
| 2016/0166800 A1 | 6/2016 | Tomes et al. |
| 2016/0193444 A1 | 7/2016 | Tomes et al. |
| 2016/0228676 A1 | 8/2016 | Glithero et al. |
| 2016/0243332 A1 | 8/2016 | Portela et al. |
| 2017/0056122 A1 | 3/2017 | Ramsey |
| 2017/0056125 A1 | 3/2017 | Garza et al. |
| 2017/0086746 A1 | 3/2017 | Ofek et al. |
| 2017/0106165 A1 | 4/2017 | Holmes |
| 2017/0202699 A1 | 7/2017 | Zani et al. |
| 2017/0216557 A1 | 8/2017 | Kearns et al. |
| 2017/0216558 A1 | 8/2017 | Hughett et al. |
| 2017/0231804 A1 | 8/2017 | Miller et al. |
| 2017/0232226 A1 | 8/2017 | Loui et al. |
| 2017/0296282 A1 | 10/2017 | Turturro et al. |
| 2017/0296283 A1 | 10/2017 | Turturro et al. |
| 2017/0296284 A1 | 10/2017 | Turturro et al. |
| 2017/0319183 A1 | 11/2017 | Tomes et al. |
| 2017/0349305 A1 | 12/2017 | Tomes et al. |
| 2017/0368302 A1 | 12/2017 | Brooks et al. |
| 2018/0001052 A1 | 1/2018 | Lockwood et al. |
| 2018/0056030 A1 | 3/2018 | Tomes et al. |
| 2018/0057196 A1 | 3/2018 | Tomes et al. |
| 2018/0206933 A1 | 7/2018 | Healey et al. |
| 2018/0221564 A1 | 8/2018 | Patel et al. |
| 2019/0151195 A1 | 5/2019 | Tomes et al. |
| 2020/0353204 A1 | 11/2020 | Glithero et al. |
| 2020/0360103 A1 | 11/2020 | Knapp et al. |
| 2021/0196922 A1 | 7/2021 | Hughett, Sr. |
| 2023/0226310 A1 | 7/2023 | Hughett, Sr. |
| 2023/0310795 A1 | 10/2023 | Hughett, Sr. |

FOREIGN PATENT DOCUMENTS

| | | |
|---|---|---|
| DE | 102007003223 B4 | 12/2009 |
| EP | 1301782 A1 | 4/2003 |
| EP | 1595561 A2 | 11/2005 |
| EP | 1731189 A1 | 12/2006 |
| FR | 2780274 A1 | 12/1999 |
| FR | 2873929 A1 | 2/2006 |
| GB | 2365342 A | 2/2002 |
| JP | S50-149175 A | 11/1975 |
| JP | 2002-136597 A | 5/2002 |
| JP | 2005-506110 A | 3/2005 |
| JP | 2007-229520 A | 9/2007 |
| JP | 2007-319535 A | 12/2007 |
| JP | 2010-200809 A | 9/2010 |
| JP | 2011-520578 A | 7/2011 |
| WO | 9106255 A1 | 5/1991 |
| WO | 9607364 A1 | 3/1996 |
| WO | 02/004942 A1 | 1/2002 |
| WO | 02064078 A1 | 8/2002 |
| WO | 2002083021 A1 | 10/2002 |
| WO | 2004005157 A1 | 1/2004 |
| WO | 2005/027767 A1 | 3/2005 |
| WO | 2006114466 A1 | 11/2006 |
| WO | 2007/045943 A1 | 4/2007 |
| WO | 08033873 A2 | 3/2008 |
| WO | 2008139852 A1 | 11/2008 |
| WO | 2015/057999 A1 | 4/2015 |
| WO | 2015057999 | 4/2015 |
| WO | 2017147067 A1 | 8/2017 |
| WO | 2018044772 A1 | 3/2018 |
| WO | 2018057835 A1 | 3/2018 |
| WO | 2018/183752 A1 | 10/2018 |
| WO | 2018/190865 A1 | 10/2018 |
| WO | 2019/209867 A1 | 10/2019 |
| WO | 2019246307 A1 | 12/2019 |

OTHER PUBLICATIONS

Arrow, "Arrow Trauma Products" brochure, 2000.

AU 2014337176 filed Mar. 15, 2016 Examination Report dated Aug. 1, 2018.

Bardex I.C. Complete Care StateLock Device 350 ml Urine Meter Foley Tray with Bacteriostatic Collection System, Directions for Use; Dated 2006.

Bardex I.C. Infection Control 350 ml Urine Meter Foley Tray, Directions for Use; Dated 2006.

Bardex I.C. Infection Control Foley Tray, Directions for Use; Dated 2006.

C.R. Bard, Inc; "A few important words about Catheter Care"; Dated 2001.

CN 201480057141.5 filed Apr. 18, 2016 Office Action dated Dec. 4, 2018.

EP 14853869.7 filed Mar. 31, 2016 Extended European Search Report dated Aug. 4, 2017.

EP 14853869.7 filed Mar. 31, 2016 Office Action dated Mar. 13, 2019.

JP 2016-523921 filed Apr. 15, 2016 Office Action dated Jul. 11, 2018.

Ortega, R. et. al. "Female Urethral Catheterization", N Engl J Med 2008; 358: e15. Apr. 3, 2008.

PCT/US14/60963 filed Oct. 16, 2014 International Search Report and Written Opinion dated Jan. 14, 2015.

(56) References Cited

OTHER PUBLICATIONS

PCT/US2017/027628 filed Apr. 14, 2017 International Search Report and Written Opinion dated Jul. 17, 2017.
PCT/US2018/025260 filed Mar. 29, 2018 International Search Report and Written Opinion dated Jun. 7, 2018.
Request for Inter partes Review of U.S. Pat. No. 8,631,935, filed Dec. 30, 2014.
Thomson et. al. "Male Urethral Catheterization", N Engl J Med 2006; 354: e22. May 25, 2006.
U.S. Appl. No. 15/029,613, filed Apr. 14, 2016 Final Office Action dated Apr. 10, 2019.
U.S. Appl. No. 15/029,613, filed Apr. 14, 2016 Non-Final Office Action dated Nov. 29, 2018.
U.S. Appl. No. 15/487,297, filed Apr. 13, 2017 Non-Final Office Action dated Apr. 5, 2019.
U.S. Appl. No. 15/487,297, filed Apr. 13, 2017 Restriction Requirement dated Nov. 29, 2018.
U.S. Appl. No. 16/639,059, filed Feb. 13, 2020 Restriction Requirement dated Oct. 13, 2021.
"Uniting the best of Healthcare" http://ghx.com/about/, last accessed 2019.
Addison, R. et al., "Catheter Care," Royal College of Nursing, London (2008).
American Journal of Infection Control. vol. 46 (2018) SI6-67.
C. R. Bard Urological Drainage, https://www.crbard.com/medical/Professionals/Product-Concentrations/Urological-Drainage, last accessed 2019.
California Department of Public Health, "Catheter-Associated Urinary Tract Infection (CAUTI) Prevention" (2015).
Dept. of Health and Human Services, "Action Plan to Prevent Healthcare-Associated Infections." (2009).
Dobkin et al., "Myth and Measurement—The Case of Medical Bankruptcies," 378 New Eng. J. Med., 1076-78 (2018).
Ellen Elpern, et al., "Prevention of Catheter-Associated Urinary Tract Infections in Adults," 36 Critical Care Nurse, 9 (2016).
Foxman, B. "Epidemiology of Urinary Tract Infections: Incidence, Morbidity, and Economic Costs." The American Journal of Medicine, 113 Suppl 1A (2002).
Gould et al., "Catheter-associated Urinary Tract Infection (CAUTI) Toolkit," Centers for Disease Control and Prevention Devision of Healthcare Quality Promotion. (2009).
Gould et al., "Guideline for Prevention of Catheter Associated Urinary Tract Infections," Centers for Disease Control Healthcare Infection Control Practices Advisory Committee, (2009).
Greene, L. et al. "Guide to the Elimination of Catheter-Associated Urinary TractInfections (CAUTIs): Developing and Applying Facility-Based Prevention Interventions in Acute and Long-Term Care Settings," Association for Professionals in Infection Control and Epidemiology, (2008).
Jacobsen, S.M. et al., "Complicated Catheter-Associated UrinaryTract Infections Due to *Escherichia coli* and Proteus mirabilis", 21 Clinical Microbiology Reviews 1, 26-59 (Jan. 2008).

Jennifer A Meddings, "Implementing Strategies to Reduce Hospital-Acquired Catheter-Associated Urinary Tract Infection," Wound, Ostomy and Continence Nurses Society, www.catheterout.org, (Jun. 2010).
Linda Kohn et al., eds., "To Err is Human: Building a Safer Health System," Institute of Medicine (US), (2000).
Lo, E. et al., "Strategies to Prevent Catheter-Associated Urinary Tract Infections in Acute Care Hospitals," Infection Control and Hospital Epidemiology. 29, S41-S50 (2008).
Madeo M. et al., "Reducing the risks associated with urinary catheters." Nursing Standard, vol. 23, No. 29, 47-55 (2009).
Male Catheter Insertion Video, Uploaded to YouTube on Feb. 7, 2008, Parts 1 and 2. https://www.youtube.com/watch?v=ISBAya_5cIM (Last accessed Feb. 26, 2020).
Norman, Donald A., The Design of Everyday Things, 2002 ed. (Excerpt).
Saint et al., "Catheter-Associated Urinary Tract Infection and the Medicare Rule Changes," Annals of Internal Medicine, Jun. 16, 2009.
Steultjens, M.P.M. et al., "Range of joint motion and disability in patients with osteoarthritis of the knee or hip," Rheumatology, Bristish Society for Rheumatology. (2000).
The Joint Commision on National Patient Safety, "2012 National Patient Safety Goals: Hospital accreditation Program." (2012).
Urological Drainage website, http://m.bardmedical.com/products/urological-drainage/, last accessed 2019.
U.S. Appl. No. 15/487,297, filed Apr. 13, 2017 Final Office Action dated Feb. 21, 2020.
PCT/US20/35371 filed May 29, 2020 International Search Report and Written Opinion dated Sep. 14, 2020.
U.S. Appl. No. 15/487,297, filed Apr. 13, 2017 Advisory Action dated Apr. 28, 2020.
U.S. Appl. No. 15/487,297, filed Apr. 13, 2017 Notice of Allowance dated Oct. 2, 2020.
U.S. Appl. No. 15/487,297, filed Apr. 13, 2017 Restriction Requirement dated Jun. 11, 2020.
PCT/US2019/038051 filed Jun. 19, 2019 International Preliminary Report on Patentability dated Dec. 22, 2020.
PCT/US2019/038051 filed Jun. 19, 2019 International Search Report and Written Opinion dated Aug. 29, 2019.
Raheem, "Application of Plastics and Paper as Food Packaging Materials" An Overview, 2017, Emirates Journal of Food and Agriculture, vol. 25, pp. 177-188 (Year: 2017).
U.S. Appl. No. 16/639,059, filed Feb. 13, 2020 Notice of Allowance dated Jul. 1, 2022.
U.S. Appl. No. 17/058,067, filed Nov. 23, 2020 Non-Final Office Action dated Jul. 7, 2022.
U.S. Appl. No. 16/639,059, filed Feb. 13, 2020 Non-Final Office Action dated Feb. 8, 2022.
U.S. Appl. No. 17/982,288, filed Nov. 7, 2022 Advisory Action dated Jul. 28, 2023.
U.S. Appl. No. 17/982,288, filed Nov. 7, 2022 Non-Final Office Action dated Aug. 28, 2023.
U.S. Appl. No. 18/207,075, filed Jun. 7, 2023 Notice of Allowance dated Aug. 11, 2023.

* cited by examiner

CATHETER INSERTION-TRAY SYSTEMS AND METHODS THEREOF

PRIORITY

This application is a U.S. national stage application of International Application No. PCT/US2018/025260, filed Mar. 29, 2018, which claims the benefit of priority to U.S. Provisional Application No. 62/479,687, filed Mar. 31, 2017, each of which is incorporated by reference in its entirety into this application.

BACKGROUND

Catheterization packages including catheter-insertion trays are generally designed and optimized for a catheter-insertion process by one person such as a nurse, wherein the nurse stands on one side of a patient's bed and performs all preparation and insertion steps of the catheter-insertion process from one side of a catheter-insertion tray. By the very nature of the one-person catheter-insertion process, the nurse can introduce unwanted contamination to sterile parts of the catheter-insertion tray and cause unintended complications subsequent to the catheter-insertion process. As such, the catheter-insertion process can benefit from certain measures to ensure a sterile technique. Provided herein in some embodiments are systems and methods that address the foregoing.

SUMMARY

Provided herein in some embodiments is a catheterization package including a catheterization tray and contents for a catheterization procedure. The catheterization tray can include a structural configuration for maintaining a sterile field about a patient throughout the catheterization procedure, the sterile field including at least a portion of the tray. The structural configuration of the tray can provide a sterile side of the tray designated for a first person performing sterile steps of the catheterization procedure in the sterile field. The structural configuration of the tray can also provide a non-sterile side of the tray designated for either the first person or a second person performing non-sterile steps of the catheterization procedure outside the sterile field. The contents for the catheterization procedure can include a perineal care kit, two or more pairs of gloves, and a drainage system including a catheter.

Also provided herein in some embodiments is a catheterization package including a catheterization tray and contents for a catheterization procedure. The catheterization tray can include a structural configuration for maintaining a sterile field about a patient throughout the catheterization procedure, the sterile field including at least a portion of the tray. The structural configuration of the tray can provide a sterile side of the tray designated for a first person performing sterile steps of the catheterization procedure in the sterile field. The structural configuration of the tray can also provide a non-sterile side of the tray designated for either the first person or a second person performing non-sterile steps of the catheterization procedure outside the sterile field. The structural configuration can include at least a partition separating the sterile and non-sterile sides of the tray along a length of the tray in a medial portion of the tray. The contents for the catheterization procedure can include a perineal care kit configured for cleaning a patient's peri-urethral area, two or more pairs of sterile gloves, and a drainage system. The drainage system can include a catheter, including a drainage catheter, such as a urinary catheter, for example, a Foley catheter; drainage tubing; and a drainage bag configured for draining material such as urine from a patient.

Also provided herein in some embodiments is a method for a catheterization package including molding a catheterization tray for the catheterization package. The catheterization tray can include a structural configuration for maintaining a sterile field about a patient throughout a catheterization procedure, the sterile field including at least a portion of the tray. The structural configuration of the tray can provide a sterile side of the tray designated for a first person performing sterile steps of the catheterization procedure in the sterile field. The structural configuration of the tray can also provide a non-sterile side of the tray designated for either the first person or a second person performing non-sterile steps of the catheterization procedure outside the sterile field.

Also provided herein in some embodiments is a method of a catheterization package including unwrapping the catheterization package to reveal a catheterization tray, removing a first set of contents for a catheterization procedure from a non-sterile side of the tray, and removing a second set of contents for the catheterization procedure from a sterile side of the tray. Unwrapping the catheterization package to reveal the catheterization tray can include revealing a structural configuration of the tray for maintaining a sterile field about a patient throughout a catheterization procedure, the sterile field including at least a portion of the tray. The structural configuration of the tray can include a sterile side of the tray designated for a first person performing sterile steps of the catheterization procedure in the sterile field. The structural configuration of the tray can also provide a non-sterile side of the tray designated for either the first person or a second person performing non-sterile steps of the catheterization procedure outside the sterile field. Removing the first set of contents for the catheterization procedure from the non-sterile side of the tray can include removing an underpad and a fenestrated drape from the non-sterile side of the catheterization tray. Removing the second set of contents for the catheterization procedure from the sterile side of the tray can include removing a drainage system including a urinary catheter, drainage tubing, and a drainage bag from the sterile side of the catheterization tray.

These and other features of the concepts provided herein may be better understood with reference to the drawings, description, and appended claims.

DRAWINGS

FIG. 1 provides a schematic illustrating a first layer of a catheterization package for use by one or more persons in accordance with some embodiments.

Figure 2:
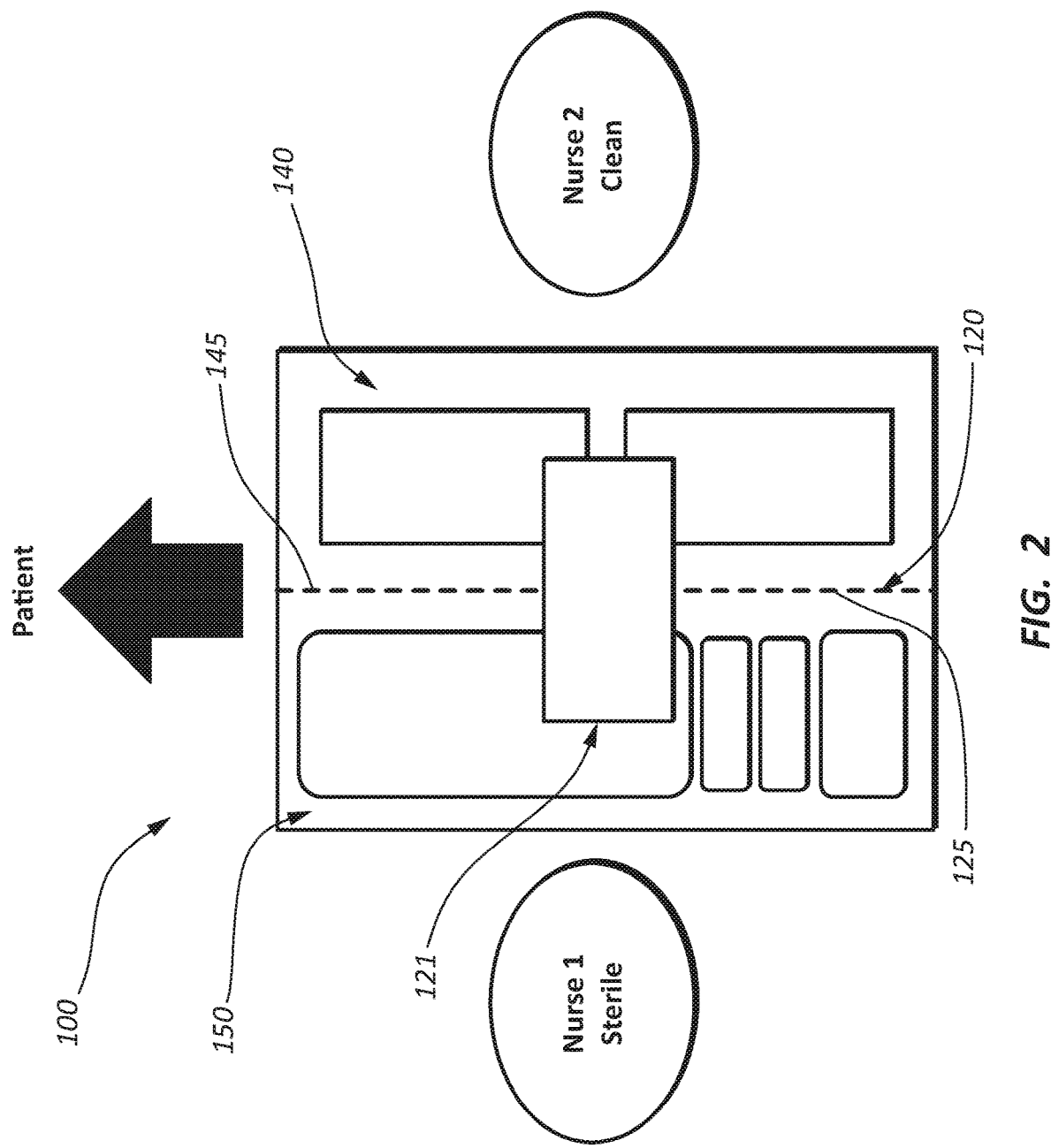

FIG. 2 provides a schematic illustrating a second layer of the catheterization package of FIG. 1 in accordance with some embodiments.

Figure 3:
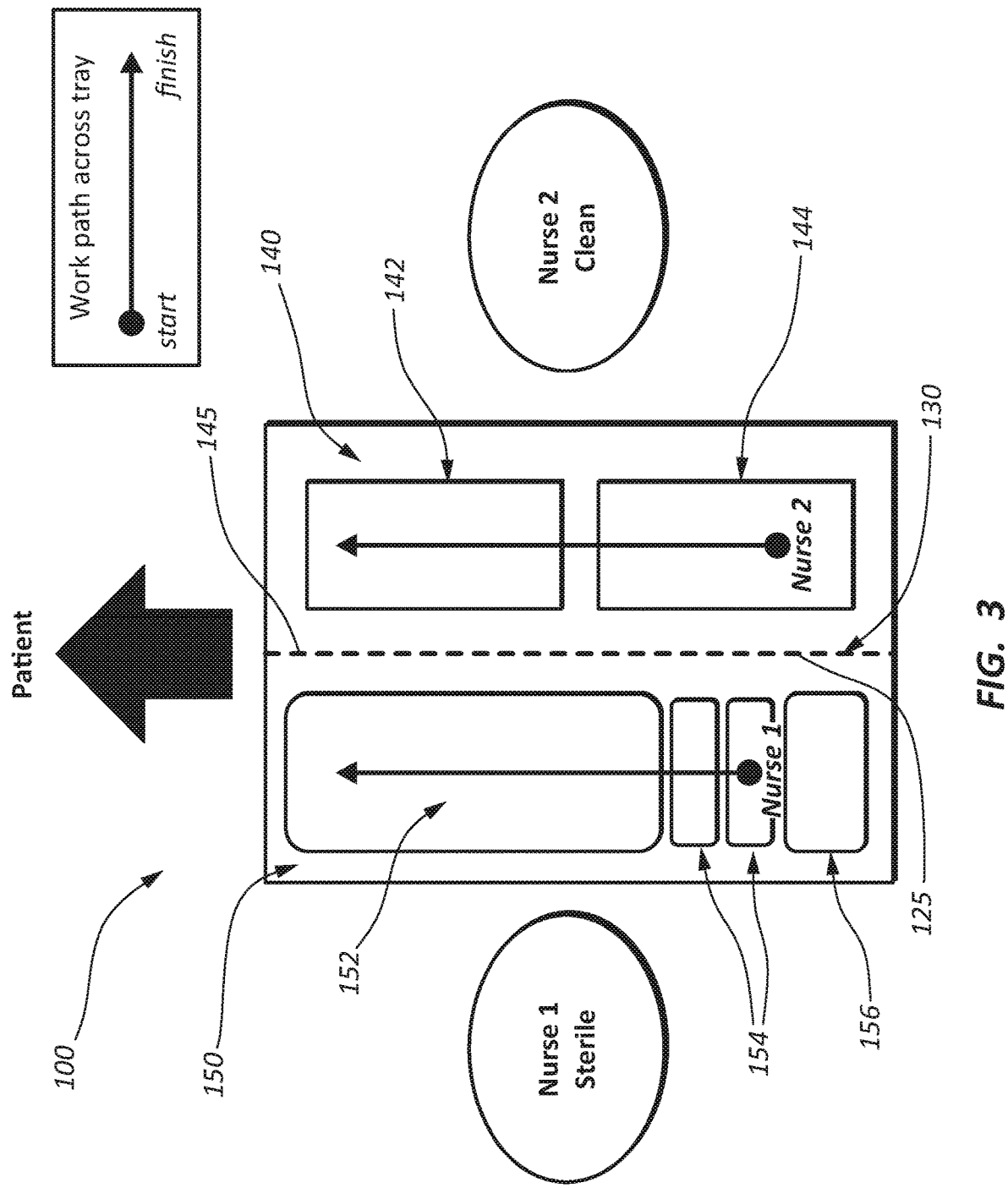

FIG. 3 provides a schematic illustrating a third layer of the catheterization package of FIG. 1 in accordance with some embodiments.

Figure 4:
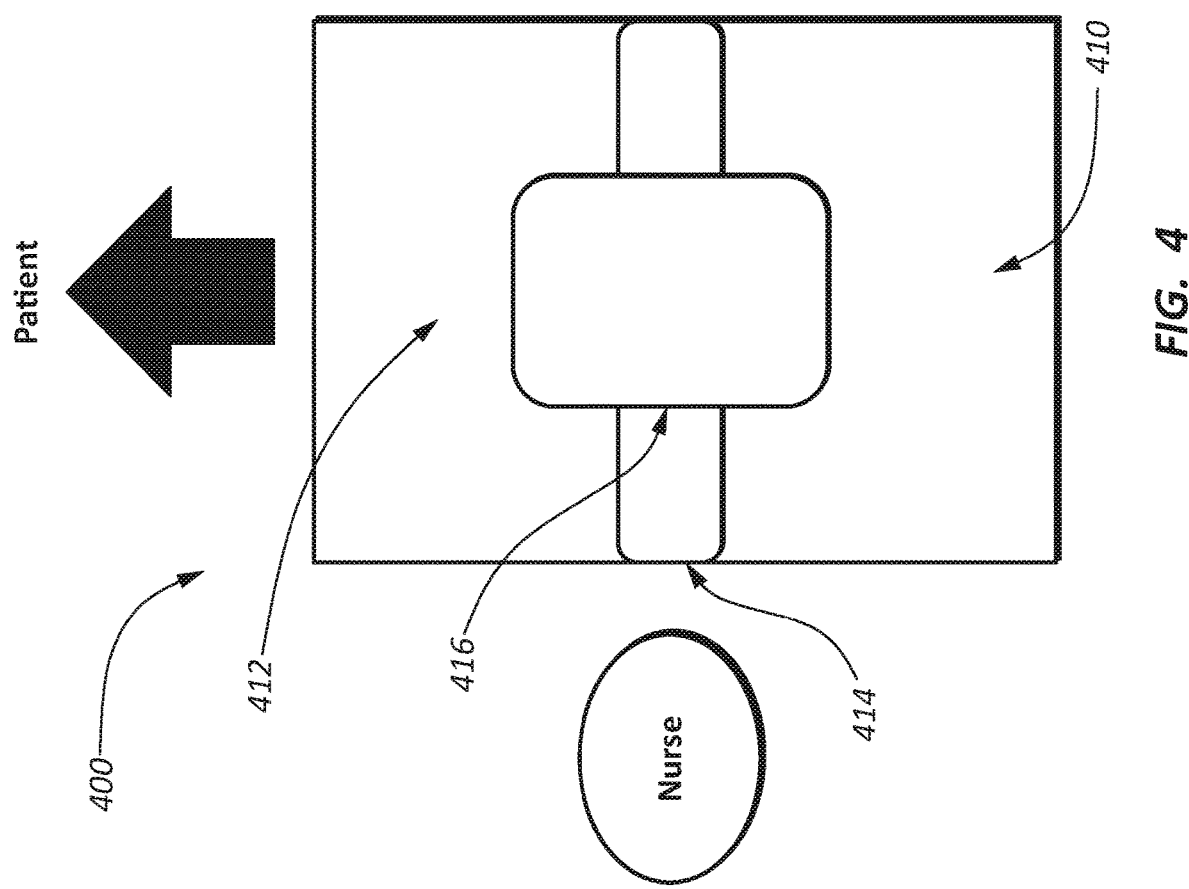

FIG. 4 provides a schematic illustrating a first layer of a one-person catheterization package.

Figure 5:
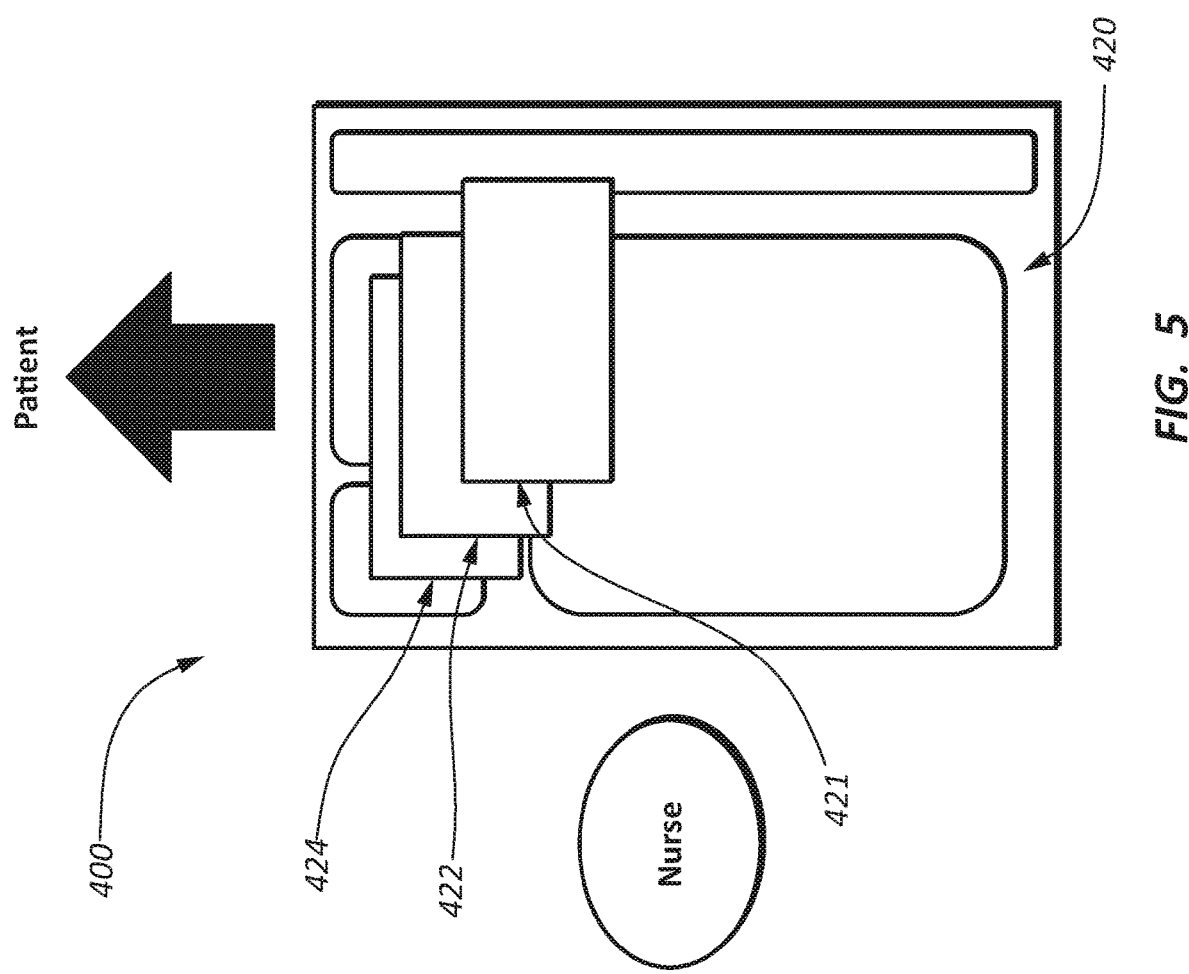

FIG. 5 provides a schematic illustrating a second layer of the one-person catheterization package of FIG. 4.

Figure 6:
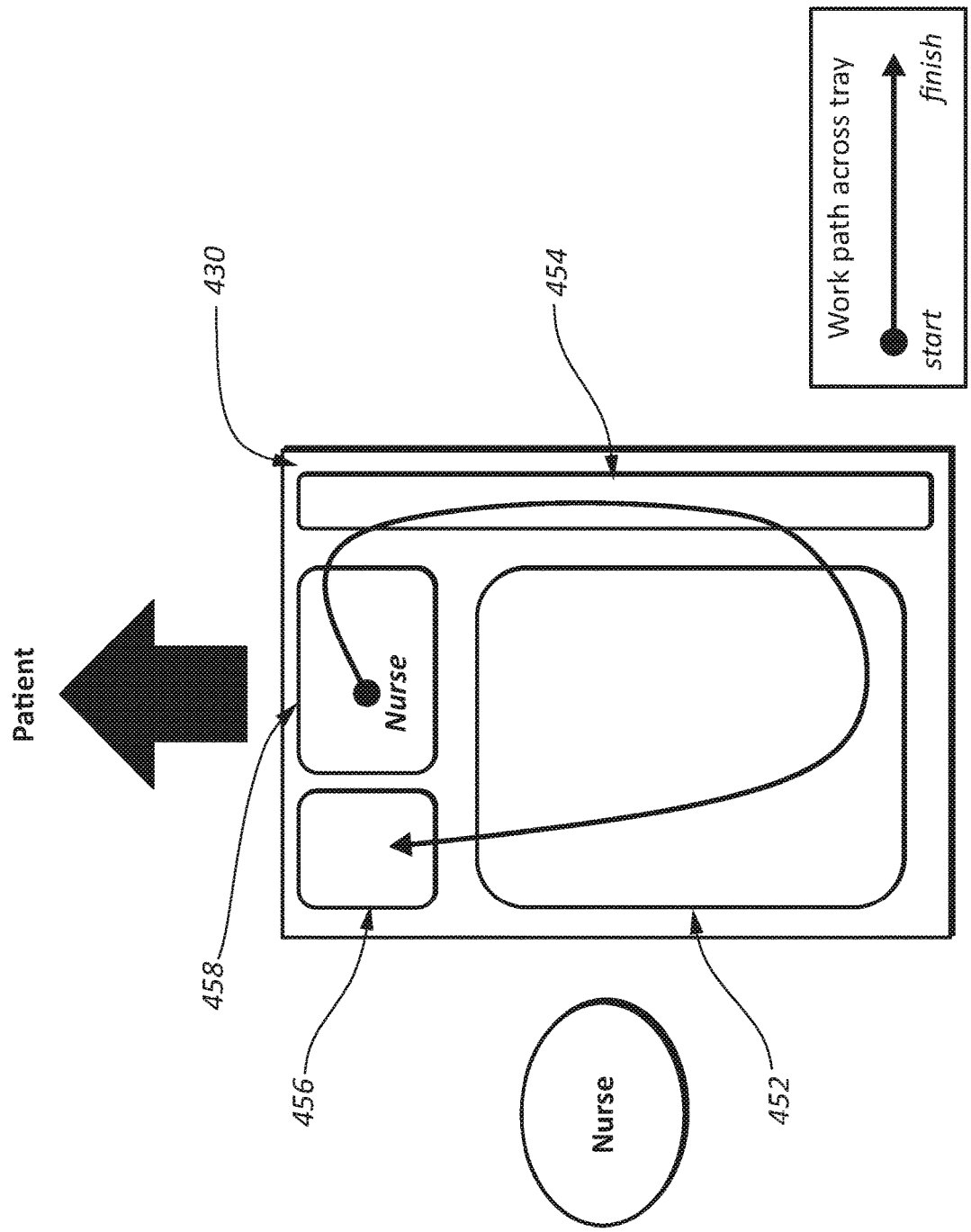

FIG. 6 provides a schematic illustrating a third layer of the one-person catheterization package of FIG. 4.

DETAILED DESCRIPTION

Before some particular embodiments are provided in greater detail, it should be understood that the particular embodiments provided herein do not limit the scope of the concepts provided herein. It should also be understood that a particular embodiment provided herein can have features that can be readily separated from the particular embodiment and optionally combined with or substituted for features of any of a number of other embodiments provided herein.

Regarding terminology used herein, it should also be understood the terminology is for the purpose of describing some particular embodiments, and the terminology does not limit the scope of the concepts provided herein. Unless indicated otherwise, ordinal numbers (e.g., first, second, third, etc.) are used to distinguish or identify different features or steps in a group of features or steps, and do not supply a serial or numerical limitation. For example, "first," "second," and "third" features or steps need not necessarily appear in that order, and the particular embodiments including such features or steps need not necessarily be limited to the three features or steps. It should also be understood that, unless indicated otherwise, any labels such as "left," "right," "front," "back," "top," "bottom," "forward," "reverse," "clockwise," "counter clockwise," "up," "down," or other similar terms such as "upper," "lower," "aft," "fore," "vertical," "horizontal," "proximal," "distal," and the like are used for convenience and are not intended to imply, for example, any particular fixed location, orientation, or direction. Instead, such labels are used to reflect, for example, relative location, orientation, or direction. It should also be understood that the singular forms of "a," "an," and "the" include plural references unless the context clearly dictates otherwise.

Unless defined otherwise, all technical and scientific terms used herein have the same meaning as commonly understood by those of ordinary skill in the art.

Catheterization packages including catheter-insertion trays are generally designed and optimized for a catheter-insertion process by one person such as a nurse, wherein the nurse stands on one side of a patient's bed and performs all preparation and insertion steps of the catheter-insertion process from one side of a catheter-insertion tray. By the very nature of the one-person catheter-insertion process, the nurse can introduce unwanted contamination to sterile parts of the catheter-insertion tray and cause unintended complications subsequent to the catheter-insertion process.

Sterile technique in the catheter-insertion process can be compromised when previously sterile, gloved hands having touched a non-sterile patient cross above a sterile surface, re-enter a sterile field, or touch sterile components such as a sterile catheter. For example, sterile technique can be compromised when sterile-gloved hands approach or touch a patient during perineal care ("pericare"), draping, or cleansing, each of which can require patient retraction or positioning (e.g., moving skin, genitalia, etc. into proper position so catheterization is possible). It can be difficult to eliminate such sterile technique-compromising activities because these activities are often necessary to a one-person catheter-insertion process with existing one-person catheterization packages—not to mention such compromises in sterile technique often go unnoticed.

FIG. 4 provides a schematic illustrating a first layer 410 of a one-person catheterization package 400.

As shown, the catheterization package 400 includes the first layer 410 including a wrap 412, a belly band 414 around the wrap 412, and a perineal care kit 416. The one-person catheterization package 400 is designed such that one nurse starts a catheterization procedure on a patient from one side of the catheterization package 400 or a catheterization tray thereof, which is typically biased to right-handed nurses. Clean gloves from a wall or elsewhere in a room are donned for the catheterization procedure and a perineal-urethral cleansing of the patient is subsequently performed. After the cleansing, the gloves are removed, and the nurse uses hand sanitizer to clean his or her hands prior to unwrapping the catheterization package 400.

FIG. 5 provides a schematic illustrating a second layer 420 of the one-person catheterization package 400 of FIG. 4.

As shown, the catheterization package 400 includes the second layer 420 including a pair of gloves 421, an underpad 422, and a fenestrated drape 424 upon unwrapping the catheterization package 400. Once unwrapped, a sterile portion of the catheterization package 400 is exposed and, therefore, sterile gloves are donned. Continuing with the catheterization procedure, the nurse places the underpad 422 under the patient followed by the fenestrated drape 424 over the patient, each of which carries with it a contamination risk from manipulating the patient.

FIG. 6 provides a schematic illustrating a third layer 430 of the one-person catheterization package 400 of FIG. 4.

As shown, the catheterization package 400 includes the third layer 430 including a catheter assembly 452, syringes 454, a sample container 456, and a preparative solution 458 subsequent to removing contents of the second layer 420. Continuing with the catheterization procedure, the nurse cleans the patient with the preparation solution 458, which further carries with it a contamination risk from manipulating the patient. Subsequently, the nurse prepares a catheter of the catheter assembly with lubricant and water. Note that this requires the nurse to move potentially contaminated hands across a sterile field above the catheter assembly, as well as even touch the catheter with contaminated hands. The nurses potentially contaminating work path is shown in FIG. 6 by an arrow starting from a section of the tray including the preparative solution 458 to a section of the tray including the sample container 456.

In view of the foregoing, the catheter-insertion process can benefit from certain measures to ensure a sterile technique in the catheter-insertion process. For example, the catheter-insertion process can benefit from more than one person or health care provider to ensure a sterile technique in the catheter-insertion process. Provided herein in some embodiments are a catheterization package and a catheterization procedure thereof designed to ensure a sterile technique in the catheter-insertion process. In some embodiments, the catheterization package and a catheterization procedure thereof are designed for catheter insertion by more than one person or health care provider. The present disclosure, however, is also applicable to catheter insertion by a single healthcare provider, such as a nurse.

For example, in some embodiments is a catheterization package is provided including a catheterization tray and contents for a catheterization procedure. The catheterization tray can include a structural configuration for maintaining a sterile field about a patient throughout the catheterization procedure, the sterile field including at least a portion of the tray. The structural configuration of the tray can provide a sterile side of the tray designated for a first person performing sterile steps of the catheterization procedure in the sterile field. The structural configuration of the tray can also provide a non-sterile side of the tray designated for either the first person or a second person performing non-sterile steps of the catheterization procedure outside the sterile field. The contents for the catheterization procedure can include a perineal care kit, two or more pairs of gloves, and a drainage system including a catheter.

Such a catheterization package and catheterization tray can facilitate a sterile catheterization procedure by isolating sterile contents of the catheterization package and steps of the catheterization procedure from previously sterile contents of the catheterization package and non-sterile steps of the catheterization procedure, thereby reducing or eliminating compromises in sterile technique.

FIG. 1 provides a schematic illustrating a first layer 110 of a catheterization package 100 for use by one or more persons in accordance with some embodiments.

As shown, the catheterization package 100 can include the first layer 110 a sterile wrap 112, a belly band 114 configured to hold the sterile wrap, and a perineal care kit 116 including hand sanitizer, and, optionally, two or more pairs of gloves.

The sterile wrap can be a central supply room ("CSR") wrap and the belly band 114 can be configured to hold the sterile wrap around the catheterization tray. The perineal care kit 116 can be located outside the sterile wrap optionally with at least one package of hand sanitizer. A first pair of gloves of the two or more pairs of gloves can be located outside the sterile wrap, or the first pair of gloves of the two or more pairs of gloves can be located inside the sterile wrap. Alternatively, a first pair of gloves of the two or more pairs of gloves can be located outside the sterile wrap and a second pair of gloves of the two or more pairs of gloves can be located inside the sterile wrap.

FIG. 2 provides a schematic illustrating a second layer 120 of the catheterization package 100 of FIG. 1 in accordance with some embodiments.

As shown, the catheterization package 100 can include the second layer 120 including a catheterization tray, optionally, two or more pairs of gloves 121 if not part of the first layer 110 or in addition thereto, a clean or non-sterile side 140 of the tray, and a sterile side 150 of the tray.

It should be understood that while the non-sterile side 140 of the tray is referred to herein as "non-sterile," "non-sterile" is intended to refer to a particular side of the tray that need not remain sterile or is otherwise outside the sterile field during the catheterization process. Contents of the catheterization package 100 on the non-sterile side 140 can be sterile as packaged in the catheterization package 100.

The tray can have a structural configuration including at least a partition 125 separating the sterile and non-sterile sides of the tray along a length of the tray in a medial portion of the tray; however, the structural configuration of the tray is not limited thereto for separating the sterile and non-sterile sides of the tray. The structural configuration of the tray can also be such that the contents in the tray can be layered in the tray in step with the sterile and the non-sterile steps of the catheterization procedure.

The tray can also include instructions for the catheterization procedure imprinted directly on the tray, at least some of which instructions are revealed in step with the sterile and the non-sterile steps of the catheterization procedure as the contents in the tray are removed. Because the structural configuration of the tray accommodates layered contents for the catheterization procedure, the tray is also configured such that removal of the contents from the tray can reveal the instructions (e.g., the instructions imprinted on the tray), additional contents for the catheterization procedure, or a combination of the instructions and the additional contents in step with the sterile and the non-sterile steps of the catheterization procedure.

The tray can be configured with a bias toward right-handed or left-handed catheter insertion by swapping the non-sterile side 140 of the tray and the sterile side 150 of the tray. For example, the tray of FIG. 2 can accommodate a left-handed catheter insertion, but by swapping the non-sterile side 140 of the tray and the sterile side 150 of the tray, the tray can accommodate a right-handed catheter insertion.

The tray can be of any size necessary for a catheterization procedure including those requiring multiple drapes or even walleted drapes.

FIG. 3 provides a schematic illustrating a third layer 130 of the catheterization package 100 of FIG. 1 in accordance with some embodiments.

As shown, the catheterization package 100 can include the third layer 130 including the non-sterile side 140 of the tray with an underpad 142 and a fenestrated drape 144. The third layer 130 of the catheterization package 100 can further include the sterile side 150 of the tray with a catheter assembly or drainage system 152, syringes 154, and a sample container 156. The arrow for Nurse 1 and the arrow for Nurse 2 show work paths for how contents of the catheterization package 100 can be removed without compromising sterile technique and the sterile field of which the sterile side 150 of the tray is part. It should be understood that the arrows for Nurses 1 and 2 merely show work paths across the catheterization package 100. Nurse 1 and Nurse 2 need not reflect different nurses. Nurse 1 and Nurse 2 can be the same nurse at different times or different nurses at the same or different times.

With respect to the non-sterile side 140 of the tray, the tray can further include a skin-preparation kit including a package of an antiseptic (e.g., an iodophor such as iodopovidone, tincture of iodine, aqueous iodine, etc.) and one or more swabs configured for preparing a patient for inserting a catheter of the catheter assembly.

With respect to the sterile side 150 of the tray, the drainage system 152 thereof can include a catheter, including a drainage catheter, such as a urinary catheter, for example, a Foley catheter; drainage tubing; and a drainage bag configured for draining material such as urine from a patient. For example, the drainage system 152 can be configured for draining urine from a patient's bladder and include a Foley catheter, drainage tubing, and a drainage bag. At least one syringe of the syringes 154 can include a syringe of sterile saline for inflating a balloon of a Foley catheter, and at least one other syringe of the syringes 154 can include a syringe (or another dispensing container) containing lubricant for lubricating the Foley catheter in accordance with the catheterization procedure.

In accordance with FIGS. 1-3, a catheterization package can include, in some embodiments, a catheterization tray and contents for a catheterization procedure. The catheterization tray can include a structural configuration for maintaining a sterile field about a patient throughout the catheterization procedure, the sterile field including at least a portion of the tray. The structural configuration of the tray can provide a sterile side of the tray designated for a first person performing sterile steps of the catheterization procedure in the sterile field. The structural configuration of the tray can also provide a non-sterile side of the tray designated for either the first person or a second person performing non-sterile steps of the catheterization procedure outside the sterile field. The contents for the catheterization procedure can include a perineal care kit, two or more pairs of gloves, and a drainage system including a catheter.

In such embodiments of the catheterization package, the structural configuration of the tray can include at least a partition (e.g., a partition molded into the tray itself) separating the sterile and non-sterile sides of the tray along a length of the tray in a medial portion of the tray; however, the structural configuration of the tray is not limited thereto for separating the sterile and non-sterile sides of the tray. The structural configuration of the tray can also be such that the contents in the tray for catheterization procedure can be layered to reveal the instructions, additional contents for catheterization procedure, or a combination of the instructions and the additional contents in step with the sterile and the non-sterile steps of the catheterization procedure. The tray can also include instructions for the catheterization procedure imprinted directly on the tray, at least some of which instructions are revealed in step with the sterile and the non-sterile steps of the catheterization procedure as the contents in the tray are removed.

Further in accordance with FIGS. 1-3, a catheterization package can include, in some embodiments, a catheterization tray and contents for a catheterization procedure. The catheterization tray can include a structural configuration for maintaining a sterile field about a patient throughout the catheterization procedure, the sterile field including at least a portion of the tray. The structural configuration of the tray can provide a sterile side of the tray designated for a first person performing sterile steps of the catheterization procedure in the sterile field. The structural configuration of the tray can also provide a non-sterile side of the tray designated for the first person or a second person performing non-sterile steps of the catheterization procedure outside the sterile field. The structural configuration can include at least a partition (e.g., a partition molded into the tray itself) separating the sterile and non-sterile sides of the tray along a length of the tray in a medial portion of the tray. The contents for the catheterization procedure can include a perineal care kit configured for cleaning a patient's peri-urethral area, two or more pairs of sterile gloves, and a drainage system. As provided herein, the drainage system can include a Foley catheter, drainage tubing, and a drainage bag configured for draining urine from a patient's bladder.

In such embodiments of the catheterization package, the contents for the catheterization procedure can further include a syringe of sterile saline configured for inflating a balloon of the Foley catheter, a container (e.g., syringe) containing lubricant configured for lubricating the Foley catheter, and a sterile sample container configured for holding a patient's urine sample. The sterile side of the tray can be configured to include the drainage system, the syringe of sterile saline, the container containing lubricant, and the sample container.

In such embodiments of the catheterization package, the contents for the catheterization procedure can further include a waterproof underpad configured for placement under a patient and a fenestrated drape configured for placement over a patient. The non-sterile side of the tray can be configured to include the underpad and the fenestrated drape.

In such embodiments of the catheterization package, the contents for the catheterization procedure can further include a skin-preparation kit including a package of an antiseptic (e.g., an iodophor such as iodopovidone, tincture of iodine, aqueous iodine, etc.) and one or more swabs configured for preparing a patient for inserting the Foley catheter. The non-sterile side of the tray is configured to include the skin-preparation kit.

In such embodiments of the catheterization package, the tray can include instructions for the catheterization procedure imprinted directly on the tray, at least some of which instructions are revealed in step with the sterile and the non-sterile steps of the catheterization procedure as the contents in the tray are removed. The structural configuration of the tray can be such that the contents in the tray can be layered to reveal the instructions, additional contents, or a combination of the instructions and the additional contents in step with the sterile and the non-sterile steps of the catheterization procedure.

In such embodiments of the catheterization package, the catheterization package can further comprise a sterile wrap and a belly band configured to hold the sterile wrap around the catheterization tray. The perineal care kit can be located outside the sterile wrap with a package of hand sanitizer. In addition, a first pair of gloves of the two or more pairs of gloves can be located outside the sterile wrap. Additionally or alternatively, a second pair of gloves of the two or more pairs of gloves can be located inside the sterile wrap.

Manufacturing

A catheterization package such at the catheterization package 100 of FIGS. 1-3 can be manufactured by initially creating a catheterization tray for the catheterization package and subsequently filling the tray with contents for a catheterization procedure.

With respect to creating the tray, the tray can be created by molding any of a number of moldable materials into a form of the tray. Again, the catheterization tray can include a structural configuration for maintaining a sterile field about a patient throughout the catheterization procedure, the sterile field including at least a portion of the tray. The structural configuration of the tray can provide a sterile side of the tray designated for a first person performing sterile steps of the catheterization procedure in the sterile field. The structural configuration of the tray can also provide a non-sterile side of the tray designated for either the first person or a second person performing non-sterile steps of the catheterization procedure outside the sterile field. For example, the structural configuration of the tray can include at least a partition separating the sterile and non-sterile sides of the tray along a length of the tray in a medial portion of the tray. A tray with such a structural configuration can be created by molding any of the number of moldable materials in a molding process selected from, but not limited to, compression molding, injection molding, thermoforming, and a combination thereof.

With respect to filling the tray with contents for the catheterization procedure, the tray can be filled by placing an underpad and a fenestrated drape in the non-sterile side of the catheterization tray. The tray can be further filled by placing a drainage system in the sterile side of the catheterization tray, the drainage system including, for example, a Foley catheter, drainage tubing, and a drainage bag.

Subsequent to creating the tray and filling the tray with contents for the catheterization procedure, the tray can be wrapped in a sterile wrap. A belly band can be added to hold the sterile wrap around the catheterization tray. Lastly, a perineal care kit and a package of hand sanitizer can be added outside the sterile wrap resulting in a catheterization package.

Use

A catheterization package such as the catheterization package 100 of FIGS. 1-3 can be used by one or more persons such as by one or more nurses (e.g., two nurses) for one or more steps of a catheterization procedure.

A catheterization procedure using the catheterization package 100 of FIGS. 1-3 can include unwrapping the catheterization package to reveal a catheterization tray, removing a first set of contents for the catheterization procedure from a non-sterile side of the tray, and removing a second set of contents for the catheterization procedure from a sterile side of the tray. Unwrapping the catheterization package to reveal the catheterization tray can include revealing a structural configuration of the tray for maintaining a sterile field about a patient throughout a catheterization procedure, the sterile field including at least a portion of the tray. Again, the structural configuration of the tray can include a sterile side of the tray and a non-sterile side of the tray, wherein the sterile side of the tray is designated for a first person performing sterile steps of the catheterization procedure in the sterile field, and wherein the non-sterile side of the tray is designated for either the first person or a second person performing non-sterile steps of the catheterization procedure outside the sterile field. Removing the first set of contents for the catheterization procedure from the non-sterile side of the tray can include removing an underpad and a fenestrated drape from the non-sterile side of the catheterization tray. (See work path of Nurse 2 in FIG. 3, wherein Nurse 2 removes the first set of contents from the tray.) Removing the second set of contents for the catheterization procedure from the sterile side of the tray can include removing a drainage system including, for example, a Foley catheter, drainage tubing, and a drainage bag from the sterile side of the catheterization tray. (See work path of Nurse 1 in FIG. 3, wherein Nurse 1 removes the second set of contents from the tray.)

The catheterization procedure can further include removing a third set of contents for the catheterization procedure from an outside of the catheterization package prior to unwrapping the catheterization package. Removing the third set of contents for the catheterization procedure from the catheterization package can include removing a perineal care kit and a package of hand sanitizer from outside a sterile wrap wrapping the catheterization package prior to unwrapping the catheterization package. The configuration of the catheterization package enables performance of the non-sterile step of removing the perineal care kit and the hand sanitizer from the catheterization package while maintaining the sterile field.

The catheterization procedure can further include placing the underpad under the patient, cleaning a peri-urethral area of the patient with the perineal care kit, and placing the fenestrated drape over the patient. The structural configuration of the tray enables performance of the non-sterile steps of placing the underpad under the patient, cleaning the peri-urethral area of the patient with the perineal care kit, and placing the fenestrated drape over the patient by the second person while maintaining the sterile field. One example of a suitable perineal care kit that can be used in accordance with the present disclosure is described in PCT Publication No. WO 2016/126555, the disclosure of which is incorporated herein by reference in its entirety.

The catheterization procedure can further include preparing the patient and the catheter for catheterization and subsequently catheterizing the patient. Preparing the patient for catheterization can include preparing the patient with a skin-preparation kit of the catheterization package, the skin-preparation kit including an antiseptic (e.g., an iodophor such as iodopovidone, tincture of iodine, aqueous iodine, etc.) and on or more swabs. Preparing the catheter for catheterization can include lubricating the catheter with a lubricant from a container containing the lubricant from the catheterization package. The structural configuration of the tray enables performance of the sterile steps of removing the drainage system including the catheter from the catheterization tray, preparing the patient and the catheter for catheterization, and catheterizing the patient by the first person while maintaining the sterile field.

In view of the foregoing, the catheterization package 100 of FIGS. 1-3 and the catheterization tray thereof set up two fields including one sterile field and one non-sterile field such that at least one person designated as a sterile nurse and at least one other person designated as a non-sterile nurse (optionally, the sterile nurse at a different time) can respectively ensure non-compromising sterile technique in a catheter-insertion process. The sterile nurse's responsibility is to manage the sterile parts of the catheterization package as well as insertion of the catheter. The non-sterile nurse's responsibility is to manage the non-sterile components (e.g., previously sterile components that need not remain sterile) of the catheter-insertion process as well some patient preparation (e.g., cleaning the peri-urethral area of the patient with the perineal care kit) and draping. As such, the non-sterile nurse cleans, touches, and positions the patient while the sterile nurse maintains the sterile field and inserts the catheter with sterile-gloved hands that have not been compromised.

The configuration of the catheterization package and the structural configuration of the catheterization tray facilitate the roles of the sterile nurse and the non-sterile nurse. As shown in FIGS. 1-3, the tray is designed to be used from two separate sides with appropriate contents for the catheterization procedure on each side of the two separate sides to be accessed by the appropriate person (e.g., the sterile nurse and the non-sterile nurse or one nurse acting as both the sterile nurse and the non-sterile nurse at different times). For example, the perineal care kit (if not packaged outside the catheterization package), one or more pairs of gloves, and the skin-preparation kit (e.g., the antiseptic and swabs) can be located on the non-sterile side of the tray while one or more other pairs of gloves and the drainage system including the catheter can be located on the sterile side of the tray. The non-sterile nurse on the right-hand side of the catheterization package 100 of FIG. 1 is designated for cleaning a patient's peri-urethral area with gloves (e.g., the gloves from first layer 110 or second layer 120). If two nurses, both nurses subsequently remove their gloves and clean their hands with the hand sanitizer, optionally packaged in individualized packages of hand sanitizer. In accordance with FIG. 3, the sterile nurse proceeds to remove the drainage system from the sterile side of the tray and prepare the catheter with lubricant and water with sterile-gloved hands. Meanwhile, the non-sterile nurse proceeds to place the underpad, place the fenestrated drape, and apply the antiseptic (e.g., iodopovidone) with the swabs to clean the patient. The non-sterile nurse can then manipulate the patient as required for catheter insertion, after which the sterile nurse can insert the catheter. Note that this does not require any potentially contaminated hands to cross over into the sterile field or touch sterile contents for the catheterization procedure located in the sterile field.

While some particular embodiments have been provided herein, and while the particular embodiments have been provided in some detail, it is not the intention for the particular embodiments to limit the scope of the concepts presented herein. Additional adaptations and/or modifications can appear to those of ordinary skill in the art, and, in broader aspects, these adaptations and/or modifications are encompassed as well. Accordingly, departures may be made from the particular embodiments provided herein without departing from the scope of the concepts provided herein.

What is claimed is:

1. A catheterization package, comprising:
   sterile contents for a catheterization procedure, including:
      a perineal care kit;

two or more pairs of gloves; and
a drainage system including a catheter; and
a sterile catheterization tray with a structural configuration for maintaining a sterile field including at least a portion of the catheterization tray throughout the catheterization procedure, the structural configuration of the catheterization tray including:
a first side of the catheterization tray configured as a sterile side of the catheterization tray for a first person performing sterile steps of the catheterization procedure in the sterile field,
a second side of the catheterization tray configured as a non-sterile side of the catheterization tray for either the first person or a second person performing non-sterile steps of the catheterization procedure outside the sterile field, and
a partition separating the first side and the second side of the catheterization tray along a length of the catheterization tray from one end of the catheterization tray to an opposite end of the catheterization tray, wherein the contents for the catheterization procedure are disposed in the catheterization tray for removal therefrom by the first person or the first person and the second person during the catheterization procedure in accordance with sterile and non-sterile work paths respectively across the first and second sides of the catheterization tray.

2. The catheterization package according to claim 1, further comprising a sterile wrap and a belly band configured to hold the sterile wrap around the catheterization tray, wherein the perineal care kit is located outside the sterile wrap with a package of hand sanitizer.

3. The catheterization package according to claim 2, wherein at least a first pair of gloves of the two or more pairs of gloves is located outside the sterile wrap.

4. The catheterization package according to claim 2, wherein at least a first pair of gloves of the two or more pairs of gloves is located inside the sterile wrap.

5. The catheterization package according to claim 1, wherein the contents for the catheterization procedure further include:
a syringe of sterile saline;
a container containing lubricant; and
a sample container, wherein the first side of the catheterization tray is configured to include the drainage system, the syringe of sterile saline, the container containing lubricant, and the sample container.

6. The catheterization package according to claim 1, wherein the contents for the catheterization procedure further include:
an underpad; and
a fenestrated drape, wherein the second side of the catheterization tray is configured to include the underpad and the fenestrated drape.

7. A catheterization package, comprising:
sterile contents for a catheterization procedure, including:
a perineal care kit configured for cleaning a patient's peri-urethral area;
two or more pairs of sterile gloves; and
a drainage system configured for draining urine from a patient's bladder including a urinary catheter, drainage tubing, and a drainage bag; and
a sterile catheterization tray with a structural configuration for maintaining a sterile field including at least a portion of the catheterization tray throughout the catheterization procedure, wherein the structural configuration of the catheterization tray includes:
a first side of the catheterization tray configured as a sterile side of the catheterization tray for a first person performing sterile steps of the catheterization procedure in the sterile field;
a second side of the catheterization tray configured as a non-sterile side of the catheterization tray for either the first person or a second person performing non-sterile steps of the catheterization procedure outside the sterile field; and
a partition separating the first side and the second side of the catheterization tray along a length of the catheterization tray from one end of the catheterization tray to an opposite end of the catheterization tray, wherein the contents for the catheterization procedure are disposed in the catheterization tray for removal therefrom by the first person, or the first person, and the second person, during the catheterization procedure in accordance with sterile and non-sterile work paths respectively across the first and second sides of the catheterization tray.

8. The catheterization package according to claim 7, wherein the contents for the catheterization procedure further include:
a syringe of sterile saline configured for inflating a balloon of the urinary catheter;
a container containing lubricant configured for lubricating the urinary catheter; and
a sterile sample container configured for holding a patient's urine sample, wherein the first side of the catheterization tray is configured to include the drainage system, the syringe of sterile saline, the container containing lubricant, and the sample container.

9. The catheterization package according to claim 7, wherein the contents for the catheterization procedure further include:
a waterproof underpad configured for placement under a patient; and
a fenestrated drape configured for placement over a patient, wherein the second side of the catheterization tray is configured to include the waterproof underpad and the fenestrated drape.

10. The catheterization package according to claim 7, wherein the contents for the catheterization procedure further include a skin-preparation kit including a package of an antiseptic and one or more swabs configured for preparing a patient for inserting the urinary catheter, wherein the second side of the catheterization tray is configured to include the skin-preparation kit.

11. The catheterization package according to claim 7, wherein the catheterization tray includes instructions for the catheterization procedure imprinted directly on the catheterization tray, at least some of which instructions are revealed in step with the sterile and the non-sterile steps of the catheterization procedure as the contents in the catheterization tray are removed.

12. The catheterization package according to claim 7, further comprising a sterile wrap and a belly band configured to hold the sterile wrap around the catheterization tray, wherein the perineal care kit is located outside the sterile wrap with a package of hand sanitizer.

13. The catheterization package according to claim 12, wherein at least a first pair of gloves of the two or more pairs of gloves is located outside the sterile wrap.

14. The catheterization package according to claim 12, wherein at least a first pair of gloves of the two or more pairs of gloves is located inside the sterile wrap.

15. A method of using a catheterization package, comprising:
unwrapping the catheterization package to reveal a sterile catheterization tray with a structural configuration for maintaining a sterile field about a patient including at least a portion of the catheterization tray throughout a catheterization procedure, wherein the structural configuration of the catheterization tray includes:
a first side of the catheterization tray configured as a sterile side of the catheterization tray for a first person performing sterile steps of the catheterization procedure in the sterile field,
a second side of the catheterization tray configured as a non-sterile side of the catheterization tray for either the first person or a second person performing non-sterile steps of the catheterization procedure outside the sterile field, and
a partition separating the first side and the second side of the catheterization tray along a length of the catheterization tray from one end of the tray to an opposite end of the catheterization tray, wherein sterile contents for the catheterization procedure are disposed in the catheterization tray for removal therefrom by the first person or the first person and the second person during the catheterization procedure in accordance with sterile and non-sterile work paths respectively across the first side and the second side of the catheterization tray;
removing an underpad and a fenestrated drape from the second side of the catheterization tray; and
removing a drainage system including a urinary catheter, drainage tubing, and a drainage bag from the first side of the catheterization tray.

16. The method of using the catheterization package according to claim 15, further comprising:
removing a perineal care kit and a package of hand sanitizer from outside a sterile wrap of the catheterization package; and
cleaning a peri-urethral area of the patient with the perineal care kit.

17. The method of using the catheterization package according to claim 15, further comprising:
placing the underpad under the patient; and
placing the fenestrated drape over the patient, wherein the structural configuration of the catheterization tray enables performance of the non-sterile steps of placing the underpad under the patient and placing the fenestrated drape over the patient by either the first person or the second person while maintaining the sterile field.

18. The method of using the catheterization package according to claim 15, further comprising:
preparing the patient and the urinary catheter for catheterization; and
catheterizing the patient, wherein the structural configuration of the catheterization tray enables performance of the sterile steps of removing the drainage system from the catheterization tray, preparing the patient and the urinary catheter for catheterization, and catheterizing the patient by the first person while maintaining the sterile field.

19. A method for manufacturing a catheterization package, comprising:
molding a catheterization tray for the catheterization package, wherein the catheterization tray includes a structural configuration for maintaining a sterile field about a patient including at least a portion of the catheterization tray throughout a catheterization procedure, wherein the structural configuration of the catheterization tray includes:
a first side of the catheterization tray configured as a sterile side of the catheterization tray for a first person performing sterile steps of the catheterization procedure in the sterile field;
a second side of the catheterization tray configured as a non-sterile side of the catheterization tray for either the first person or a second person performing non-sterile steps of the catheterization procedure outside the sterile field; and
a partition separating the first side and the second side of the catheterization tray along a length of the catheterization tray from one end of the catheterization tray to an opposite end of the catheterization tray;
disposing contents for the catheterization procedure in the catheterization tray for removal therefrom by the first person or the first person and the second person during the catheterization procedure in accordance with sterile and non-sterile work paths respectively across the first and second sides of the catheterization tray; and
sterilizing the catheterization package.

20. The method for manufacturing the catheterization package according to claim 19, wherein disposing the contents for the catheterization procedure in the catheterization tray includes placing an underpad and a fenestrated drape in the second side of the catheterization tray.

21. The method for manufacturing the catheterization package according to claim 19, further comprising:
placing a drainage system including a urinary catheter, drainage tubing, and a drainage bag in the first side of the catheterization tray when disposing the contents for the catheterization procedure in the catheterization tray; and
wrapping a sterile wrap around the catheterization tray.

22. The method for manufacturing the catheterization package according to claim 21, further comprising placing a perineal care kit and a package of hand sanitizer outside the sterile wrap of the catheterization package.

* * * * *